(12) United States Patent
Bourgeois et al.

(10) Patent No.: US 10,646,704 B2
(45) Date of Patent: May 12, 2020

(54) METHOD OF FORMING A MEDICAL TUBE

(71) Applicant: Tekni-Plex, Inc., Wayne, PA (US)

(72) Inventors: Philip D. Bourgeois, Perrysburg, OH (US); Munish Shah, Sylvania, OH (US)

(73) Assignee: Tekni-Plex, Inc., Wayne, PA (US)

(*) Notice: Subject to any disclaimer, the term of this patent is extended or adjusted under 35 U.S.C. 154(b) by 139 days.

(21) Appl. No.: 15/872,042

(22) Filed: Jan. 16, 2018

(65) Prior Publication Data

US 2018/0133449 A1 May 17, 2018

Related U.S. Application Data

(63) Continuation of application No. 13/354,029, filed on Jan. 19, 2012, now abandoned.

(51) Int. Cl.
| | |
|---|---|
| *A61M 39/08* | (2006.01) |
| *B32B 1/08* | (2006.01) |
| *B32B 27/30* | (2006.01) |
| *B32B 27/32* | (2006.01) |
| *B32B 27/40* | (2006.01) |
| *F16L 11/10* | (2006.01) |
| *F16L 11/12* | (2006.01) |

(Continued)

(52) U.S. Cl.
CPC .............. *A61M 39/08* (2013.01); *B29C 48/09* (2019.02); *B32B 1/08* (2013.01); *B32B 27/308* (2013.01); *B32B 27/32* (2013.01); *B32B 27/40* (2013.01); *F16L 11/10* (2013.01); *F16L 11/12* (2013.01); *B29C 48/18* (2019.02); *B29C 48/22* (2019.02); *B32B 2535/00* (2013.01); *B32B 2597/00* (2013.01); *F16L 11/04* (2013.01)

(58) Field of Classification Search
CPC ........ A61M 39/08; B32B 27/40; B32B 27/32; B32B 27/308; B32B 1/08; B32B 2597/00; B32B 2535/00; B29C 48/09; B29C 48/18; B29C 48/22

See application file for complete search history.

(56) References Cited

U.S. PATENT DOCUMENTS

| | | |
|---|---|---|
| 4,211,741 A | 7/1980 | Ostoich |
| 4,627,844 A | 12/1986 | Schmitt et al. |

(Continued)

FOREIGN PATENT DOCUMENTS

| | | |
|---|---|---|
| DE | 202004000533 U1 | 3/2004 |
| EP | 0244960 A1 | 11/1987 |

(Continued)

OTHER PUBLICATIONS

Int'l. Preliminary Report on Patentability dated Sep. 22, 2014 in Int'l. Application No. PCT/US2013/049097.

(Continued)

*Primary Examiner* — Jeffrey M Wollschlager
(74) *Attorney, Agent, or Firm* — Polsinelli, PC

(57) ABSTRACT

Tubing comprising an inner layer, an outer layer and a middle layer, wherein the inner layer comprises a polyethylene, the outer layer comprises a thermoplastic polyurethane and the middle layer comprises an ethylene ethyl acrylate copolymer or an ethylene methyl acrylate copolymer or an anhydride grafted ethylene methyl acrylate copolymer, a copolymer of two or more of the acrylate copolymers or a mixture of two or more thereof.

9 Claims, 1 Drawing Sheet

(51) Int. Cl.
*B29C 48/09* (2019.01)
*F16L 11/04* (2006.01)
*B29C 48/18* (2019.01)
*B29C 48/22* (2019.01)

(56) References Cited

U.S. PATENT DOCUMENTS

| | | | |
|---|---|---|---|
| 4,948,643 A | | 8/1990 | Mueller |
| 5,052,444 A | | 10/1991 | Messerly et al. |
| 5,215,450 A | * | 6/1993 | Tamari ............... A61M 1/0031 |
| | | | 138/119 |
| 5,570,711 A | | 11/1996 | Walsh |
| 5,631,325 A | * | 5/1997 | Latiolais ............... C08F 8/44 |
| | | | 525/227 |
| 5,681,627 A | * | 10/1997 | Mueller ............... B32B 7/12 |
| | | | 428/35.2 |
| 5,733,619 A | | 3/1998 | Patel et al. |
| 5,803,130 A | * | 9/1998 | Robben ............... A61L 29/041 |
| | | | 138/137 |
| 6,074,715 A | | 6/2000 | Lind et al. |
| 6,165,166 A | | 12/2000 | Samuelson et al. |
| 6,230,749 B1 | | 5/2001 | Kertesz |
| 6,357,485 B2 | | 3/2002 | Quigley et al. |
| 6,977,105 B1 | | 12/2005 | Fujieda et al. |
| 7,647,949 B2 | | 1/2010 | Donohue et al. |
| 8,399,077 B1 | | 3/2013 | Bakele |
| 2002/0014474 A1 | | 2/2002 | Tiberghien et al. |
| 2002/0061377 A1 | | 5/2002 | Kertesz |
| 2002/0139428 A1 | | 10/2002 | Kertesz |
| 2003/0165647 A1 | | 9/2003 | Kaneko et al. |
| 2003/0208259 A1 | | 11/2003 | Penhase |
| 2004/0073192 A1 | * | 4/2004 | Flament-Garcia .... A61L 29/049 |
| | | | 604/523 |
| 2007/0119511 A1 | | 5/2007 | Donohue et al. |
| 2007/0178131 A1 | | 8/2007 | Yamada et al. |
| 2009/0087606 A1 | | 4/2009 | Julien |
| 2009/0286028 A1 | | 11/2009 | Garver |
| 2009/0317611 A1 | | 12/2009 | Mueller et al. |
| 2010/0055367 A1 | * | 3/2010 | Ohigawa ............... B32B 1/08 |
| | | | 428/36.91 |

FOREIGN PATENT DOCUMENTS

| | | |
|---|---|---|
| EP | 02449690 A1 | 11/1987 |
| EP | 1208969 A2 | 11/2000 |
| EP | 1245377 A1 | 3/2001 |
| EP | 1249336 A2 | 1/2002 |
| EP | 1468218 B1 | 1/2003 |
| EP | 2177805 A2 | 12/2009 |
| EP | 146218 A1 | 6/2012 |
| WO | 9741906 A1 | 11/1997 |
| WO | 0013896 A1 | 1/2003 |
| WO | 03064909 A1 | 8/2003 |
| WO | 2005068887 A1 | 1/2005 |
| WO | 2009001350 A1 | 12/2008 |

OTHER PUBLICATIONS

Int'l. Preliminary Report on Patentability dated Jun. 17, 2014 in Int'l. Application No. PCT/US2012/062565.
Int'l. Search Report and Written Opinion dated Sep. 27, 2013 in Int'l. Application No. PCT/US2013/049097.
Int'l. Search Report and Written Opinion dated Sep. 27, 2013 in Int'l. Applicatin No. PCT/US2013/055075.
Int'l. Search Report and Written Opinion dated Mar. 26, 2013 in Int'l. Application No. PC/US12/062565.
Communication pursuant to Article 94(3) EPC dated Mar. 30, 2017 in European Application No. 12791897.7-1664.
Communication under Rule 71(3) EPC in corresponding European application 12791897.7 dated Jun. 27, 2019.

* cited by examiner

METHOD OF FORMING A MEDICAL TUBE

FIELD OF THE INVENTION

The present invention relates to polymeric tubing typically formed by a co-extrusion process, the tubing having multiple layers of the same or different polymeric materials each layer successively adhered to each other.

Background

Tubing comprised of polymeric material is used in many industrial and commercial applications including in the medical field. Various FDA compliant plastics are used, depending upon properties desired and the intended applications. Where the tubing is used to transport fluids for in vivo treatment of human patients, selection of the polymeric materials can be a factor.

Polyvinyl chloride (PVC) is one of the most widely used plastics. While structurally stable and easily formable into desired shapes, PVC is typically manufactured using plasticizers which can migrate out of the PVC matrix into bodily fluids and has other properties not ideally suited for medical treatment applications. Likewise, due to the inherent nature of plasticized PVC tubing, there arises the potential absorption of medicines and other components of aqueous fluids used in medical treatments into the sidewall of the PVC tube. Polyurethane is potentially a substitute for PVC. However, dual layer tubing comprised of polyurethane and polyethylene suffers from the inability of the two layers to remain adhered to each other under low to moderate stress, strain or mechanical manipulation conditions. U.S. Pat. No. 4,627,844 to Schmitt ("Schmitt"), the disclosure of which is incorporated herein by reference as if fully set forth, discloses a tri-layer tube which is embodied in a commercial product sold under the trademark "SUREPATH 151" by the Natvar Division of Tekni-Plex, Inc. As disclosed in Schmitt, an outer layer of PVC and an inner fluid-contact layer of low density polyethylene (LDPE) are co-extruded with an intermediate tie layer of ethylene vinyl acetate copolymer (EVA). However, while Schmitt greatly reduces the possibility for the migration of additives from the PVC to the fluid and absorption of components from the fluid to the PVC tubing by providing a LDPE fluid-contact layer, elimination of the PVC is preferred. Other tubing configurations are disclosed in U.S. Pat. Nos. 7,647,949, 4,211,741 and U.S. Patent Publication No. 2007/0119511, the disclosures of which are incorporated by reference as if fully set forth herein.

SUMMARY OF THE INVENTION

In accordance with the invention there is provided a tubing, tube or tubular device that comprises at least three concentric layers of polymeric materials comprising an outer layer of a first selected polymeric material (typically comprised of at least about 90% by weight of a polyurethane), an inner layer of a second selected polymeric material (typically comprised of at least about 90% by weight of a polyethylene) and an intermediate layer of a third polymeric material (typically comprised of at least about 90% by weight of an acrylate containing polymer) that is disposed between and binds the inner and outer layers together by adhesion mechanisms, such as chemical adhesion. The layers of polymeric materials are co-extruded together to form the tubing such that the outer and inner layers are adhered to the intermediate or middle layer and thus adhered to each other. The tubing is formed with a central hollow channel, bore or passage that is radially surrounded and defined by the polymeric layers that act as the walls of the tubing.

The polymeric materials are preferably "contaminant free" meaning that they do not contain more than insignificant amounts of potentially unwanted materials (typically less than about out 0.5% and preferably less than about 0.2%, by weight) and/or prevent leaching or leaking of unwanted materials such as plasticizers, catalysts, monomers, metals, salts, ions or other substances that are potentially unwanted to a human being into an aqueous solution or medium with which one or the other of the three layers may come into contact during the normal course of use of the tubing in delivering aqueous fluid, such as insulin, chemotherapy drugs and other potentially unstable aqueous drug suspensions, to or from a human subject. In addition to acting as an adhesive between and adhering to the outer and inner layers, the intermediate layer prevents delamination of the outer and inner layers from the intermediate layers under conditions of relatively low to moderate stress or strain. In addition, the intermediate layer acts as a barrier to leaching or leaking of contaminants from the outer layer to or through the inner layer into the hollow central bore or passage of the tube.

Preferably the polymeric material of the outer layer is comprised of a polyurethane thermoplastic elastomeric material ("TPU"), the inner layer is comprised of a polyethylene ("PE"), typically a low density polyethylene ("LDPE"), linear low density polyethylene ("LLDPE"), high density polyethylene ("HDPE") or blends thereof, and the intermediate or middle layer is comprised of an ethylene ethyl acrylate copolymer (EEA), ethylene methyl acrylate copolymer (EMA), an anhydride grafted ethylene methyl acrylate copolymer (AEMA), a copolymer of two or more of said acrylates or a mixture of two or more of the foregoing.

With reference to FIGS. 1, 2, preferably the polyurethane outer layer 1 is between about 0.001" and about 0.025" in thickness, T3, the inner layer polyethylene layer 3 is between about 0.001" and about 0.025" in thickness, T1, and the intermediate acrylate copolymer layer 2 is between about 0.001" and about 0.025" in thickness, T2. The layers 1, 2, 3 collectively form a tubular wall surrounding and defining a central fluid flow passage 20.

Ethylene ethyl acrylate copolymers (EEA), Ethylene methyl acrylate (EMA) copolymers and anhydride grated ethylene methyl acrylate (AEMA) copolymers are elastomeric in nature and have excellent visual clarity. In a typical 3M3L co-extrusion process, TPU, EEA or EMA or AEMA and PE are melt extruded through a die head to form a tubular shaped extrudate that is then cooled through conventional water baths or water vacuum tanks and which are either subsequently wound or cut into a particular length for use. The level of elasticity and softness of the EEA, EMA AEMA or copolymer thereof is controlled through the amount of ethyl acrylate or methyl acrylate comonomer utilized with ethylene in the copolymerization process. The resulting three layer tubes manufactured by such a co-extrusion process act in a monolithic manner in that they return to close to their original shape and dimensions after being strained or stretched in a tensile manner along the longitudinal axis of the tube at a stress of up to about 55 MPa and a strain of up to about 900-950% and without any visual delaminaton between any of the layers after being submersed in water at about 60° C. for about 36 hours.

In accordance with the invention there is provided a tube comprising an inner layer, an outer layer and a middle layer, wherein the inner layer comprises a polyethylene, the outer layer comprises a thermoplastic polyurethane and the middle layer comprises an ethylene ethyl acrylate copolymer or an ethylene methyl acrylate copolymer or an anhydride grafted ethylene methyl acrylate copolymer, a copolymer of two or more of said acrylates or a mixture of two or more of the foregoing.

The inner layer typically comprises more than about 90% by weight of a polyethylene, the outer layer typically comprises more than about 90% by weight of an aromatic or aliphatic polyether based polyurethane and the middle layer typically comprises more than about 90% by weight of an ethylene ethyl acrylate copolymer.

The polyethylene typically comprises one or more of a low density polyethylene, a linear low density polyethylene and a high density polyethylene, the aromatic polyether based polyurethane typically comprises a polytetramethyleneglycol-based polyurethane and the ethylene ethyl acrylate copolymer typically comprises at least about 19.5 percent ethyl acrylate content by weight.

The inner layer typically comprises more than about 90% by weight of polyethylene, the outer layer typically comprises more than about 90% by weight of a aromatic polyether based polyurethane and the middle layer typically comprises more than about 90% by weight of an ethylene methyl acrylate copolymer.

The inner layer can comprise more than about 90% by weight of low density polyethylene (LDPE) while the outer layer comprises more than about 90% by weight of a polytetramethyleneglycol-based polyurethane and the middle layer comprises more than about 90% an anhydride grafted ethylene methyl acrylate copolymer.

Typically, the thickness of the polyurethane outer layer is between about 0.001" and about 0.025", the thickness of the inner polyethylene layer is between about 0.001" and about 0.025" and the thickness of the intermediate acrylate copolymer layer is between about 0.001" and about 0.025".

Most preferably, the inner and outer layers do not visually delaminate from each other at a stress up to of about 55 MPa and a strain of up to about 900-950% when measured by pulling a length of tubing about 2 inches in axial length along its axis using a Lloyd LR5K plus mechanical tester at a pull rate of about 12 inches/minute at ambient environmental conditions of about 72 degrees F. and about 50% relative humidity, the break point of the tubing 10 being about 57-62 MPa and about 1000-1050%.

Most preferably, the tube does not visually delaminate after being subjected to submersion in water at 60° C. for 36 hours and subsequently mechanically flattened by manual squeezing of the tube from its normal round in cross-sectional condition to a flattened or oval shape cross-sectional shape or condition.

Preferably the tube has a central axial fluid flow passage through which aqueous fluid is routed, the inner layer having a radially inner wall surface that contacts the aqueous fluid, the outer and inner layers resisting delamination from each other at a stress of up to about 55 MPa and a strain of up to about 900-950%.

In another aspect of the invention there is provided a medical tube for transport of aqueous fluid comprising:
an inner layer comprising more than about 90% by weight of a polyethylene
an outer layer comprising more than about 90% by weight of a an aromatic polyether-based polyurethane and,
a middle layer disposed between the outer and inner layers comprising more than about 90% by weight of an ethylene ethyl acrylate copolymer or an ethylene methyl acrylate copolymer or an anhydride grafted ethylene methyl acrylate copolymer, a copolymer of two or more of said acrylates or a mixture of two or more of the foregoing.

In such an embodiment, the inner and outer layers preferably do not visually delaminate from each other at a stress of up to about 55 MPa and a strain of up to about 900-950%. And such a tube preferably does not visually delaminate after being submersed in water at 60° C. for 36 hours.

In another aspect of the invention there is provided, a medical tube for transport of an aqueous fluid comprising:
an inner layer comprised of at least about 90% by weight of a polyethylene.
an outer layer comprised of at least about 90% by weight of an aromatic polyether-based polyurethane,
a middle layer disposed between the inner and outer layers comprised of at least about 90% by weight of an ethylene ethyl acrylate copolymer, an ethylene methyl acrylate copolymer, an anhydride grafted ethylene methyl acrylate copolymer, a copolymer of two or more of said acrylates or a mixture of two or more of the foregoing,
wherein said tubing does not visually delaminate after being submersed in water at 60° C. for 36 hours.

In another aspect of the invention there is provided a medical tube for transport of an aqueous fluid comprising:
an inner layer comprised of at least about 90% by weight of a low density polyethylene,
an outer layer comprised of at least about 90% by weight of a polytetramethyleneglycol-based polyurethane,
a middle layer comprised of at least about 90% by weight of an ethylene ethyl acrylate copolymer, an ethylene methyl acrylate copolymer, an anhydride grafted ethylene methyl acrylate copolymer, a copolymer of said acrylates or a mixture of two or more of the foregoing,
wherein the tubing does not visually delaminate at a stress of up to about 55 MPa and a strain of up to about 900-950%, and,
wherein the tubing does not visually delaminate after being submersed in water at 60° C. for 36 hours.

Most preferably the middle layer serves as a barrier against, prevents or substantially lessens migration of mobile moieties such as monomers, short chained polymers, ions, water, small organic molecules, metals, plasticizers, catalysts and the like between the outer and inner layers or from the outer layer into the inner layer or the central flow passage or from the central flow passage or inner layer into the outer layer.

Further in accordance with the invention there is provided a method of forming a medical tube comprising an outer layer, an innermost layer and an intermediate layer disposed between the outer layer and the innermost layer, the method comprising:
selecting a first polymeric material having a selected structural stability;
selecting a second polymeric material that is inert to aqueous fluids;
selecting a third polymeric material that readily bonds and adheres to the first and second polymeric materials on co-extrusion and cooling of the materials;
co-extruding the selected first, second and third polymeric materials to form the medical tubing in a configuration such that the outer layer comprises at least about 90% by weight of the first polymeric material, the inner layer comprises at least about 90% weight of the second polymeric material and the intermediate layer comprises at least about 90% by weight of the third polymeric material.

Preferably in such a method the first polymeric material is selected to be a polyurethane, the second polymeric material is selected to be a polyethylene and the third polymeric material is selected from the group consisting of an ethylene ethyl acrylate copolymer, an ethylene methyl acrylate copolymer, an anhydride grafted ethylene methyl acrylate copolymer, a copolymer of said acrylate copolymers or a mixture of two or more of the foregoing.

Further in accordance with the invention there is provided a method of delivering an aqueous fluid to a subject comprising;

selecting a tube comprising an inner layer, an outer layer and a middle layer, wherein the inner layer comprises a polyethylene, the outer layer comprises a thermoplastic polyurethane and the middle layer comprises an ethylene ethyl acrylate copolymer or an ethylene methyl acrylate copolymer or an anhydride grafted ethylene methyl acrylate copolymer, a copolymer of two or more of said acrylates or a mixture of two or more of the foregoing;

wherein the tube has a central fluid flow passage surrounded by the layers;

routing an aqueous fluid through the central fluid flow passage of the tube, and, delivering the aqueous fluid routed through the central fluid flow passage into a blood vessel of the subject.

In such a method, the step of selecting preferably comprises:

co-extruding the outer, inner and middle layers to form the tube such that the outer layer comprises at least about 90% by weight of the polyurethane, the inner layer comprises at least about 90% weight of the polyethylene and the intermediate layer comprises at least about 90% by weight of one or more of the acrylate copolymers.

BRIEF DESCRIPTION OF THE DRAWINGS

The drawings depict one or more embodiments of the invention that are shown by way of examples of the invention wherein.

DETAILED DESCRIPTION

Figure 1:
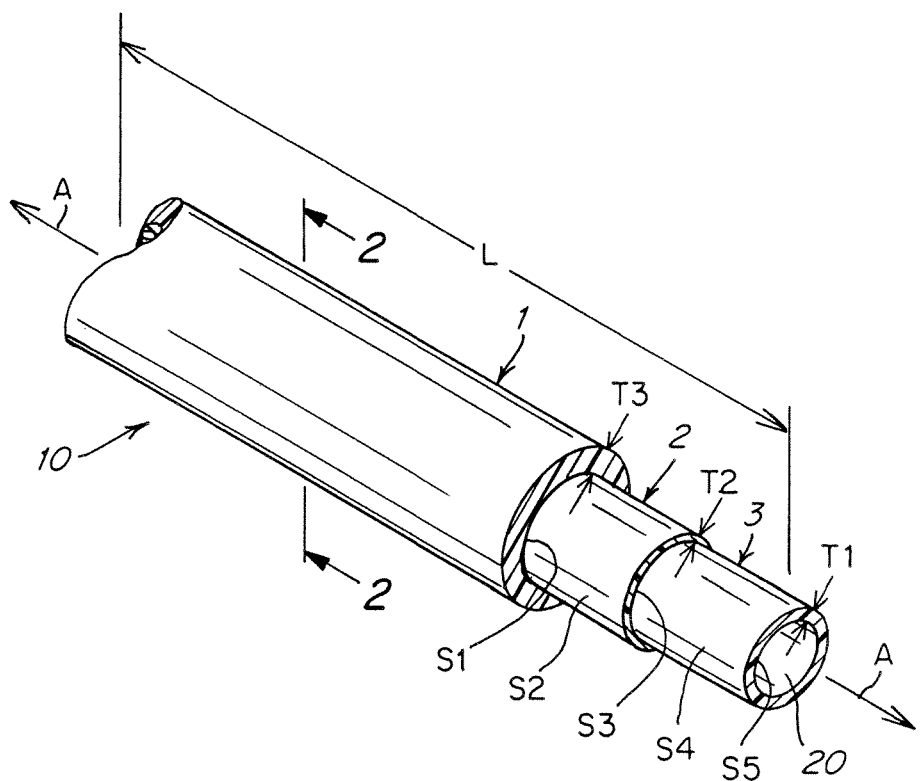
FIG. 1 is a schematic perspective view of a tri-layered tube showing the outer and middle or intermediate layers broken away in order to better illustrate the construction and arrangement of the tubing.

There is shown in FIG. 1 an embodiment of a co-extruded tri-layer tubing 10 according to the invention which comprises an outer layer 1 comprised of at least about 90% by weight of a polyurethane material, typically a polytetramethyleneglycol-based polyurethane one example of which is Lubrizol TPU Pellethane 2363-90AE, an inner fluid-contact layer 3 comprised of at least about 90% by weight of a polyethylene material, typically a low density polyethylene, one example of which is Westlake LDPE EM808AA and an intermediate bonding layer 2 comprised of at least about 90% by weight of an ethylene ethyl acrylate copolymer, an ethylene methyl acrylate copolymer, an anhydride grafted ethylene methyl acrylate copolymer, a copolymer of two or more of said acrylates or a mixture of two or more of these acrylate based compounds or compositions. One example of a suitable ethylene ethyl acrylate copolymer is Dow Amplify EA 103 (Ethylene Ethyl Acrylate being about 19.5% by weight). Examples of suitable ethylene methyl acrylate copolymers are Westlake MA SP2268 (Ethylene Methyl Acrylate being about 24% by weight), Westlake MA SP2220 (Ethylene Methyl Acrylate being about 20% by weight). One example of a suitable anhydride grafted ethylene methyl acrylate copolymer is Westlake Tymax GA 7001 (Anhydride grafted Ethylene Methyl Acrylate)

As shown in FIG. 1 the outer layer of polyurethane 1 has a radially inner facing surface S1 that binds and adheres to a radially outer facing surface S2 of the intermediate acrylate copolymer layer 2. Similarly the inner layer of polyethylene material 3 has a radially outer facing surface S4 that binds and adheres to the radially inner facing surface S3 of the intermediate acrylate copolymer layer 2. The intermediate layer 2 adheres to the outer 1 and inner 3 layers such that the layers 1 and 3 remain adhered to layer 2 and to each other when the tube 10 is subjected to a stress of up to about 55 MPa and a strain of up to about 900-950% as measured by pulling a length of tubing 10 of about 2 inches in axial length L along its axis A using a Lloyd LR5K Plus mechanical tester at a pull rate of about 12 inches/minute at ambient environmental conditions of about 72 degrees F. and about 50% relative humidity, the break point of the tubing 10 being at about 57-62 MPa and about 1000-1050%. The layers 1, 2, 3 of such tubing 10 does not visually delaminate after being subjected to submersion in water at 60° C. for 36 hours and subsequently mechanically flattened by manual squeezing of the tube from its normal round in cross-sectional condition to a flattened or oval shape cross-sectional shape or condition.

Figure 2:
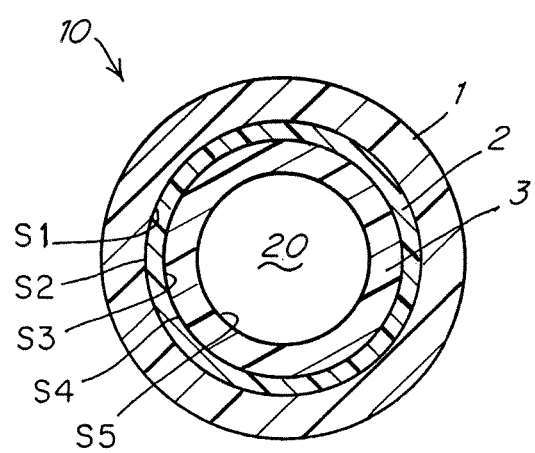
FIG. 2 is a cross-sectional view taken along lines 2-2 of the tube 10 shown in FIG. 1.

As shown in FIGS. 1 and 2, the layers 1, 2, 3 are formed into structurally stable walls that surround and enclose a central hollow fluid passage 20 through which an aqueous solution is routed and flows in an axial A direction contacting the radially inner facing surface S5 of the inner layer 3. The intermediate layer 2 binds and holds the inner 3 and outer 1 layers together.

The inner layer 3 provides a radially inner fluid-contact surface S5, the thickness, of the inner layer 3 typically ranging in cross-sectional thickness T1 of between about 0.001 inches and about 0.025 inches. The intermediate layer 2 typically ranges in cross-sectional thickness T2 of between about 0.001 inches and about 0.025 inches. The outer layer 1 typically ranges in cross-sectional thickness T3 of between about 0.001 inches and about 0.025 inches.

The polyethylene material is preferably a branched low-density polyethylene (LDPE), such as Westlake EM808, available from Westlake Chemical Corporation. The polyethylene material can be a linear low density polyethylene (LLDPE) such as Dowlex 2035G, available from the Dow Chemical Company. The polyethylene material can also be a high-density polyethylene (HDPE), such as Chevron 9506 HDPE, Chevron 9406 HDPE, and Chevron 9503 HDPE, available from Chevron Corporation.

The polyurethane elastomer (TPU) is typically the reaction product of a polyol and isocyanate and usually includes a combination of hard and soft segment domains. An aromatic polyether-based TPU or an aliphatic polyether-based TPU can be used such as a polytetramethyleneglycol-based polyurethane. Preferred, TPU's include the Pellethane 2363-80 AE series available from the Lubrizol Corporation such as Lubrizol TPU Pellethane 2363-90AE.

The respective thickness of each layer of tubing 10,20 can be controlled by the extrusion tooling utilized, such as the "Tri Die" extrusion apparatus manufactured by the Genca Division of General Cable Company, Clearwater, Fla. The extrusion apparatus is selected so as to provide a uniform thickness of the layers 1, 2, 3 along the substantial entirety of the axial length L of all three layers 1, 2, 3.

The polymeric materials of which the layers 1, 2, 3 are comprised are selected so as to be visually clear or transparent and manually flexible along and around the axis A of the tubing. The polymeric materials are also selected so as to maintain the integrity of the tubing 10 (namely delamination does not occur) and its transparency or clarity after being subjected to ethylene oxide (EtO) and gamma irradiation sterilization processes.

The foregoing description is intended to illustrate and not limit the scope of the invention, those skilled in the art will realize that equivalents thereof are contemplated by the description above and that changes and modifications may be made thereto without departing from the spirit of the invention, all such equivalents, changes and modifications falling within the scope of the claims hereof.

The invention claimed is:

1. A method of forming a visually clear or transparent and manually flexible medical tube for in vivo transport of an aqueous fluid, the method of forming comprising:
   selecting a first polymeric material that is an aromatic or aliphatic polyether based polyurethane material having a selected structural stability; and
   selecting a second polymeric material that is a polyethylene material that is inert to aqueous fluids;
   selecting a third polymeric material comprising an acrylate copolymer that is elastomeric in nature and has visual clarity selected from the group consisting of an ethylene ethyl acrylate copolymer, an anhydride grafted ethylene methyl acrylate copolymer, a copolymer of said acrylates or a mixture of two or more of the foregoing;
   co-extruding the selected first, second and third polymeric materials to form respectively adhered outer, inner and intermediate layers of the medical tube a configuration such that the outer layer comprises at least 90% by weight of the first polymeric material, the inner layer comprises at least 90% weight of the second polymeric material and the intermediate layer comprises at least 90% by weight of the third polymeric material,
   the materials being selected so as to maintain the integrity of the tube against delamination and maintain its visual clarity or transparency after being subjected to one or more of ethylene oxide and gamma irradiation sterilization, wherein the medical tube has a central axial fluid flow passage defined by a radial inner wall surface of the inner layer through which aqueous fluid is transported, and wherein the tube does not visually delaminate after being submersed in water at 60 degrees C. for 36 hours and subsequently mechanically flattened by manual squeezing of the tube from its normal round in cross-sectional condition to a flattened or oval cross-sectional shape or condition.

2. The method of claim 1 where the third polymeric material comprises an ethylene ethyl acrylate copolymer comprising at least 19.5 percent ethyl acrylate content by weight.

3. The method of claim 2 wherein, the second polymeric material comprises one or more of a low density polyethylene, a linear low density polyethylene and a high density polyethylene, and the first polymeric material comprises a polytetramethyleneglycol-based polyurethane.

4. The method of claim 1 where the inner layer comprises more than 90% by weight of low density polyethylene (LDPE), and the outer layer comprises more than 90% by weight of a polytetramethyleneglycol-based polyurethane.

5. The method of claim 1 wherein the thickness of the polyurethane outer layer is between 0.001 and 0.025 inches, the thickness of the inner polyethylene layer is between 0.001 and 0.025 inches and the thickness of the intermediate acrylate copolymer layer is between 0.001 and 0.025 inches.

6. The method of claim 1 wherein the inner and outer layers do not visually delaminate from each other at a stress up to 55 MPa and a strain up to 900-950%.

7. The method of claim 1 wherein the intermediate layer serves as a barrier against migration of mobile moieties between or from the layers and the central flow passage, wherein the mobile moieties comprise monomers, short chained polymers, ions, water, small organic molecules, metals, plasticizers, and catalysts.

8. The method of claim 1 wherein the intermediate layer comprises at least 90% by weight of an ethylene ethyl acrylate copolymer.

9. The method of claim 1 wherein:
   the inner layer comprises at least 90% by weight of a low density polyethylene,
   the outer layer comprises of at least 90% by weight of a polytetramethyleneglycol-based polyurethane,
   the intermediate layer comprises at least 90% by weight of an ethylene ethyl acrylate copolymer, and
   wherein the tube does not visually delaminate at a stress of up to 55 MPa and a strain of up to 900-950.

\* \* \* \* \*

UNITED STATES PATENT AND TRADEMARK OFFICE
CERTIFICATE OF CORRECTION

| | | |
|---|---|---|
| PATENT NO. | : 10,646,704 B2 | Page 1 of 1 |
| APPLICATION NO. | : 15/872042 | |
| DATED | : May 12, 2020 | |
| INVENTOR(S) | : Philip D. Bourgeois and Munish Shah | |

It is certified that error appears in the above-identified patent and that said Letters Patent is hereby corrected as shown below:

In the Claims

Column 7, Line 36 (Claim 1) please add --in-- after "tube"

Column 7, Line 39 (Claim 1) please add --by-- after "90%"

Signed and Sealed this
Twenty-third Day of June, 2020

Andrei Iancu
*Director of the United States Patent and Trademark Office*